United States Patent [19]

Kitamura et al.

[11] 3,970,703

[45] July 20, 1976

[54] PHENYLACETIC ACID DERIVATIVES

[75] Inventors: Shigeyoshi Kitamura; Yositosi Okuno, both of Toyonaka; Masachika Hirano, Minoo, all of Japan

[73] Assignee: Sumitomo Chemical Company, Limited, Osaka, Japan

[22] Filed: Dec. 17, 1974

[21] Appl. No.: 533,648

Related U.S. Application Data

[62] Division of Ser. No. 207,542, Dec. 13, 1971, Pat. No. 3,864,388.

[30] Foreign Application Priority Data

Dec. 29, 1970   Japan............................. 45-124365

[52] U.S. Cl........................... 260/611 A; 260/340.5
[51] Int. Cl.²......................................... C07C 43/22
[58] Field of Search..................... 260/611 A, 340.5

[56] References Cited
UNITED STATES PATENTS

| | | | |
|---|---|---|---|
| 1,931,858 | 10/1933 | Baur | 260/611 A |
| 2,487,525 | 11/1949 | Copenhauer | 260/611 A |
| 3,041,319 | 6/1962 | Abramo | 260/611 A |

*Primary Examiner*—Paul J. Killos
*Attorney, Agent, or Firm*—Stevens, Davis, Miller & Mosher

[57] ABSTRACT

A compound of the formula,

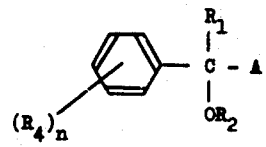

wherein $R_1$ is a $C_{1-6}$ alkyl, a $C_{2-6}$ alkenyl, a $C_{3-6}$ alkynyl, a $C_{3-6}$ cycloalkyl, benzyl, thienyl or a group of

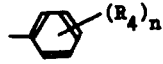

($R_4$ is hydrogen, halogen, a $C_{1-4}$ alkyl or methylenedioxy, and n is an integer of 1 to 5), $R_2$ is a $C_{1-6}$ alkyl, a $C_{3-6}$ alkenyl or a $C_{3-6}$ alkynyl, $R_3$ is a $C_{1-6}$ alkyl, a $C_{3-6}$ alkenyl or a $C_{3-6}$ alkynyl, (provided that $R_2$ is a $C_{3-6}$ alkynyl when $R_3$ is a $C_{1-6}$ alkyl), and A is a group of —COOR$_3$ or —CH$_2$OR$_3$, provided that $R_1$ is a $C_{1-6}$ alkyl, a $C_{2-6}$ alkenyl, a $C_{3-6}$ alkynyl, a $C_{3-6}$ cycloalkyl or benzyl when A is a group of —CH$_2$OR$_3$ ($R_3$ is as defined above), and $R_3$ is a $C_{4-6}$ alkenyl or a $C_{4-6}$ alkynyl when $R_1$ is a group of

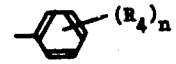

($R_4$ and $n$ are as defined above) and A is a group of —COOR$_3$, which is useful as synergist for insecticides, especially for a cyclopropane-carboxylate or a carbamate type insecticide.

2 Claims, No Drawings

PHENYLACETIC ACID DERIVATIVES

This is a division of application Ser. No. 207,542, filed Dec. 13, 1971, now U.S. Pat. No. 3,864,388.

The present invention relates to a novel phenyl acetic acid derivative and a synergist containing the same.

More particularly, this invention relates to a novel phenylacetic acid derivative represented by the formula (I),

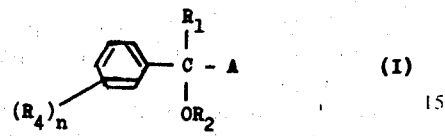

wherein $R_1$ is a $C_{1-6}$ alkyl, a $C_{2-6}$ alkenyl, a $C_{3-6}$ alkynyl, a $C_{3-6}$ cycloalkyl, benzyl, thienyl or a group of

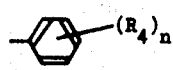

($R_4$ is hydrogen, halogen, a $C_{1-4}$ alkyl or methylenedioxy, and $n$ is an integer of 1 to 5), $R_2$ is a $C_{1-6}$ alkyl, a $C_{3-6}$ alkenyl or a $C_{3-6}$ alkynyl, $R_3$ is a $C_{1-6}$ alkyl, a $C_{3-6}$ alkenyl or a $C_{3-6}$ alkynyl, (provided that $R_2$ is a $C_{3-6}$ alkynyl when $R_3$ is a $C_{1-6}$ alkyl), and A is a group of —$COOR_3$ or —$CH_2OR_3$, provided that $R_1$ is a $C_{1-6}$ alkyl, a $C_{2-6}$ alkenyl, a $C_{3-6}$ alkynyl, a $C_{3-6}$ cycloalkyl or benzyl when A is a group of —$CH_2OR_3$ ($R_3$ is as defined above), and $R_3$ is a $C_{4-6}$ alkenyl or a $C_{4-6}$ alkynyl when $R_1$ is a group of

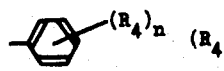

($R_4$ and $n$ are as defined above) and A is a group of —$COOR_3$, and relates to a synergist containing at least one said phenyl acetic acid derivative.

So far, it is known that sesamine and the like contained in sesame oil may be used for enhancing the insecticidal activities of pyrethroide type insecticides.

Based upon the knowledge that the sesamine contained in sesame oil has methylenedioxyphenyl group in the molecule, there have been synthesized various compounds having such group, and as the synergist for pyrethrin, there are now widely used α-[2-(butoxyethoxy)-ethoxy]-4,5-methylene-dioxy-2-propyltoluene (hereinafter referred to as piperonyl butoxide), 1,2-methylenedioxy-4-[2-(octylsulfinyl)propyl]benzene (hereinafter referred to as sulfoxide), 4-(3,4-methylenedioxy-phenyl)-5-methyl-1,3-dioxane (hereinafter referred to as safroxane), etc. There are other kinds of synergist on the market including N-(2-ethylhexyl)-bicyclo[2,2,1]-hept-5-ene-anhydro-phthalic acid-2,3-dicarboxyimide (trade mark: MGK-264, McLaughlin Gormley King Co.), and the like.

They have, however, both merits and demerits, for example, the piperonyl butoxide most widely used now among the known synergists has prominent synergistic effect on natural pyrethrin, but somewhat inferior on allethrin and other synthetic pyrethroids, and MGK-264 has more excellent synergistic effect on allethrin than that on natural pyrethrin.

Thus, an object of the present invention is to provide a novel compound having prominent synergistic effect on various cyclopropanecarboxylate type insecticides as well as on natural pyrethrin.

Another object of the present invention is to provide a novel compound having prominent synergistic effect on carbamate type insecticides.

Other objects of the present invention is to provide a process for producing such synergistic compound having low toxicity to mammals at a low production cost.

These objects can be accomplished by providing the phenylacetic acid derivative represented by the formula (I) mentioned above, and a process for producing the same which comprises reacting a compound of the formula (II), or a reactive derivative thereof,

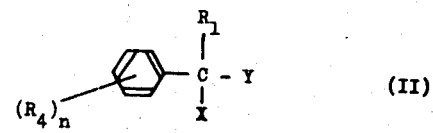

wherein $R_1$, $R_4$ and $n$ are as defined above, X is hydroxy, a halogen or —$OR_2$ ($R_2$ is as defined above) and Y is —$CH_2OH$, —$CH_2Hal$ (Hal is a halogen), —$CH_2OR_3$, —$COOR_3$ ($R_3$ is as defined above) or —$COOH$, with a compound of the formula (III), or a reactive derivative thereof,

wherein Z is hydroxy or a halogen, and $R_5$ is the same meanings as $R_1$ or $R_3$.

The process of the present invention will be illustrated in more detail.

1. The reaction between an alkali metal salt, an ammonium salt, or a salt or organic tertiary base of the acid represented by the formula (II), and the halide or tosylate of the alcohol represented by the formula (III) may be conducted in an inert solvent such as benzene, toluene, acetone and dimethylformamide at room temperature or under heating.

2. The reaction between the acid halide of the formula (II) and the alcohol of the formula (III) may be conducted in an inert solvent such as benzene and toluene using as a dehydrogen halide agent an organic tertiary base such as pyridine and triethylamine at room temperature.

3. The reaction between the acid of the formula (II) and the alcohol of the formula (III) may be conducted in an inert solvent such as benzene and toluene in the presence of a dehydrating agent at room temperature or under heating.

4. The reaction between the acid anhydride of the formula (II) and the alcohol of the formula (III) may be conducted in an inert solvent at room temperature.

5. The reaction between the α-hydroxy acid represented by the formula (II) in which both of hydroxyl and carboxyl are substituted by an alkali metal, and the halide or tosylate of the alcohol represented by the formula (III) may be conducted in an inert solvent such as benzene, toluene and dimethylformamide at room temperature or under heating.

6. The reaction between the α-haloester or the α-haloether represented by the formula (II) and the alcohol of the formula (III) in which the hydroxy is substituted by an alkali metal, may be conducted in an inert solvent such as benzene, toluene and dimethylformamide at room temperature or under heating. When the alcohol used is methanol or ethanol, if is advantageous to use methanol or ethanol as the solvent.

7. The reaction between the alcohol of the formula (II) in which the hydroxy is substituted by an alkali metal, and the halide or tosylate of the alcohol of the formula (III) may be conducted in an inert solvent such as benzene, toluene and dimethylformamide at room temperature or under heating.

According to the above mentioned process, the following compounds can be obtained.

1. Alkynyl α-alkyloxyphenyl acetates substituted by an alkyl, an alkenyl, an alkynyl, a cycloalkyl, a phenyl, a benzyl or a thienyl group at a α-position, and the acetates in which the phenyl group is substituted by at least one member of alkyl groups, halogen atoms and methylenedioxy group.

2. Alkynyl α-alkenyloxyphenylacetates substituted by an alkyl, an alkenyl, an alkynyl, a cycloalkyl, a phenyl, a benzyl or a thienyl group at α-position, and the acetates in which the phenyl group is substituted by at least one member of alkyl groups, halogen atoms and methylenedioxy group.

3. Alkynyl α-alkynyloxyphenylacetates substituted by an alkyl, an alkenyl, an alkynyl, a cycloalkyl, a phenyl, a benzyl or a thienyl group at α-position, and the acetates in which the phenyl group is substituted by at least one member of alkyl groups, halogen atoms and methylenedioxy group.

4. Alkenyl α-alkyloxyphenylacetates substituted by an alkyl, an alkenyl, an alkynyl, a cycloalkyl, a phenyl, a benzyl or a thienyl group at α-position, and the acetates in which the phenyl group is substituted by at least one member of alkyl groups, halogen atoms and methylenedioxy group.

5. Alkenyl α-alkenyloxyphenylacetates substituted by an alkyl, an alkenyl, an alkynyl, a cycloalkyl, a phenyl, a benzyl or a thienyl group at α-position, and the acetates in which the phenyl group is substituted by at least one member of alkyl groups, halogen atoms and methylenedioxy group.

6. Alkenyl α-alkynyloxyphenylacetates substituted by an alkyl, an alkenyl, an alkynyl, a cycloalkyl, a phenyl, a benzyl or a thienyl group, and the acetates in which the phenyl group is substituted by at least one member of alkyl groups, halogen atoms and methylenedioxy group.

7. Alkyl α-alkynyloxyphenylacetates substituted by an alkyl, an alkenyl, an alkynyl, a cycloalkyl, a phenyl, a benzyl, or a thienyl group at α-position, and the acetates in which the phenyl group is substituted by at least one member of alkyl groups, halogen atoms and methylenedioxy group.

8. Alkynyl α-alkoxyphenethyl ethers substituted by an alkyl, an alkenyl, an alkynyl, a cycloalkyl, or benzyl at α-position, and the ethers in which the phenyl group is substituted by at least one member of alkyl groups, halogen atoms and methylenedioxy group.

9. Alkynyl α-alkenyloxyphenethyl ethers substituted by an alkyl, an alkenyl, an alkynyl, a cycloalkyl, or benzyl at α-position, and the ethers in which the phenyl group is substituted by at least one member of alkyl groups, halogen atoms and methylenedioxy group.

10. Alkynyl α-alkynyloxyphenethyl ethers substituted by an alkyl, an alkenyl, an alkynyl, a cycloalkyl or benzyl at α-position, and the ethers in which the phenyl group is substituted by at least one member of alkyl groups, halogen atoms and methylenedioxy group.

11. Alkenyl α-alkoxyphenethyl ethers substituted by an alkyl, an alkenyl, an alkynyl, a cycloalkyl or benzyl at α-position, and the ethers in which the phenyl group is substituted by at least one member of alkyl groups, halogen atoms and methylenedioxy group.

12. Alkenyl α-alkenyloxyphenethyl ethers substituted by an alkyl, an alkyenyl, an alkynyl, a cycloalkyl or benzyl at α-position, and the ethers in which the phenyl group is substituted by at least one member of alkyl groups, halogen atoms and methylenedioxy group.

13. Alkenyl α-alkynyloxyphenethyl ethers substituted by an alkyl, an alkenyl, an alkynyl, a cycloalkyl or benzyl at α-position, and the ethers in which the phenyl group is substituted by at least one member of alkyl groups, halogen atoms and methylenedioxy group.

14. Alkyl α-alkynyloxyphenethyl ethers substituted by an alkyl, an alkenyl, an alkynyl, a cycloalkyl, or benzyl at α-position, and the ethers in which the phenyl group is substituted by at least one member of alkyl groups, halogen atoms and methylenedioxy group.

Among the present compounds mentioned above, typical examples, and formulae and physical properties thereof are enumerated as follows, and it is needless to say that the present invention is not limited only thereto.

| Compound No. | Formula | Physical property |
|---|---|---|
| 1 | Ph–C(CH$_2$CH$_2$CH$_3$)(OCH$_3$)–COOCH$_2$C≡CH<br>Propargyl α-(n-propyl)-α-methoxyphenylacetate | $n_D^{25}$ 1.5136 |
| 2 | Ph–C(CH(CH$_3$)$_2$)(OCH$_3$)–COOCH$_2$C≡CH<br>Propargyl α-(iso-propyl)-α-methoxyphenylacetate | $n_D^{25}$ 1.5071 |
| 3 | Ph–C(CH$_2$CH=CH$_2$)(OCH$_3$)–COOCH$_2$C≡CH<br>Propargyl α-allyl-α-methoxyphenylacetate | $n_D^{25}$ 1.5184 |
| 4 | Ph–C(CH$_2$CH$_2$CH=CH$_2$)(OCH$_3$)–COOCH$_2$C≡CH<br>Propargyl α-butenyl-α-methoxyphenylacetate | $n_D^{25}$ 1.5142 |
| 5 | Ph–C(CH$_2$CH=CH)(OCH$_2$CH$_3$)–COOCH$_2$C≡CH<br>Propargyl α-allyl-α-ethoxyphenylacetate | $n_D^{25}$ 1.5117 |
| 6 | Ph–C(CH$_2$CH(CH$_3$)$_2$)(OCH$_3$)–COOCH$_2$C≡CH<br>Propargyl α-(iso-butyl)-α-methoxyphenylacetate | $n_D^{25}$ 1.5112 |
| 7 | Ph–C(CH$_2$CH=CH)(OCH$_2$CH$_2$CH$_3$)–COOCH$_2$C≡CH | $n_D^{25}$ 1.5055 |

| Compound No. | Formula | Physical property |
|---|---|---|
| 8 | Propargyl α-allyl-α-(n-propyloxy)-phenylacetate<br>Ph−C(OCH₃)(CH₂CH₂CH₂CH₂CH₂CH₃)−COOCH₂C≡CH | $n_D^{25}$ 1.5166 |
| 9 | Propargyl α-(n-hexyl)-α-methoxyphenylacetate<br>Ph−C(H)(OCH₃)−COOCH₂C≡CH | $n_D^{25}$ 1.5160 |
| 10 | Propargyl α-cyclohexyl-α-methoxyphenylacetate<br>Ph−C(OCH₃)(CH₂CH=CH₂)−COOCH₂CH₂C≡CH | $n_D^{25}$ 1.5137 |
| 11 | 1-Butynyl α-allyl-α-methoxyphenylacetate<br>Ph−C(OCH₃)(CH₂Ph)−COOCH₂C≡CH | $n_D^{25}$ 1.15589 |
| 12 | Propargyl α-benzyl-α-methoxyphenylacetate<br>Ph−C(OCH₂CH₃)(CH₂Ph)−COOCH₂C≡CH | $n_D^{25}$ 1.5489 |
| 13 | Propargyl α-benzyl-α-ethoxyphenylacetate<br>Ph−C(OCH₃)(CH₂Ph)−COOCH₂CH₂CH=CH₂ | $n_D^{25}$ 1.5486 |
| 14 | Allyl α-benzyl-α-methoxyphenylacetate<br>Ph−C(OCH₃)(2-thienyl)−COOCH₂C≡CH | $n_D^{25}$ 1.5698 |
| 15 | Propargyl α-(2-thienyl)-α-methoxyphenylacetate<br>Ph−C(OCH₃)(CH₂C≡CH)−COOCH₂CH=CH₂ | $n_D^{25}$ 1.5143 |
| 16 | Allyl α-propargyl-α-methoxyphenylacetate<br>Ph−C(OCH₃)(Ph)−COOCH₂CH₂C≡CH | $n_D^{25}$ 1.5574 |
| 17 | 1-Butynyl α-phenyl-α-methoxyphenylacetate<br>Ph−C(OCH₂CH₃)(CH₂CH₂CH₃)−COOCH₂CH₂CH₂CH₂C≡CH | $n_D^{25}$ 1.4944 |
| 18 | 1-Hexynyl α-(n-propyl)-α-ethoxyphenylacetate<br>Ph−C(OCH₂CH₂C≡CH)(Ph)−COOCH₂C≡CH | $n_D^{25}$ 1.5581 |
| 19 | 1-Butynyl α-phenyl-α-(1-butynyloxy)-phenylacetate<br>Ph−C(OCH₃)(CH₂CH₂CH₃)−CH₂OCH₂C≡CH | $n_D^{25}$ 1.5085 |
| 20 | Propargyl α-(n-propyl)-α-methoxyphenethyl ether<br>Ph−C(OCH₃)(CH₂CH=CH₂)−CH₂OCH₂C≡CH | $n_D^{25}$ 1.5197 |
| 21 | Propargyl α-allyl-α-methoxyphenethyl ether<br>Ph−C(OCH₂CH₃)(CH₂CH=CH₂)−CH₂OCH₂C≡CH | $n_D^{25}$ 1.5163 |
| 22 | Propargyl α-allyl-α-ethoxyphenethyl ether<br>Ph−C(OCH₂CH=CH₂)(CH₂CH(CH₃)CH₃)−CH₂OCH₂C≡CH | $n_D^{25}$ 1.5174 |
| 23 | Propargyl α-(iso-butyl)-α-allyloxyphenethyl ether<br>Ph−C(H)(OCH₃)−CH₂OCH₂C≡CH | $n_D^{25}$ 1.5237 |
| 24 | Propargyl α-cyclohexyl-α-methoxyphenethyl ether<br>Ph−C(OCH₂C≡CH)(CH₂CH₂CH₃)−CH₂OCH₂C≡CH | $n_D^{25}$ 1.5162 |
| 25 | Propargyl α-(n-propyl)-α-propargyloxyphenethyl ether<br>Ph−C(OCH₃)(CH₂Ph)−CH₂OCH₂C≡CH | $n_D^{25}$ 1.5431 |
| 26 | Propargyl α-benzyl-α-methoxyphenethyl ether<br>Ph−C(OCH₃)(CH₂CH₂CH₃)−CH₂OCH₂CH₂C≡CH | $n_D^{25}$ 1.5150 |
| 27 | 1-Butynyl α-(n-propyl)-α-methoxyphenethyl ether<br>Ph−C(OCH₃)(CH₂CH₂CH₃)−CH−₂OCH₂CH₂CH₂CH₂C≡CH | $n_D^{25}$ 1.5132 |
| | 1-Hexyl α-(n-propyl)-α-methoxyphenethyl ether | |

The process of the present invention will be explained in more detail with reference to the following examples, which are not intended to limit the scope of the present invention.

EXAMPLE 1

A solution of 4.2 g of α-(iso-propyl)-α-methoxyphenyl acetic acid, 3.0 g of triethylamine and 2.6 of propargyl bromide in 20 cc of dimethylformamide was stirred for 2 hours, whereby white precipitates were deposited. The reaction mixture was poured in water, and the resultant was subjected to extraction with ether. The extract was washed with an aqueous solution saturated with sodium chloride and dried over anhydrous sodium sulfate, and thereafter evaporation of ether gave 4.5 g of oily propargyl α-(iso-propyl)-α-methoxyphenylacetate, $n_D^{25}$ 1.5071.

| Elementary Analysis | C (%) | H (%) |
|---|---|---|
| Calculated (as C₁₅H₁₈O₃) | 73.15 | 7.37 |
| Found | 73.42 | 7.51 |

EXAMPLE 2

Into a solution of 1.4 g of 3-butyn-1-ol and 20 g of pyridine in 20 cc of benzene, was added a solution of 4.5 g of α-allyl-α-methoxyphenyl acetic chloride in 10 cc of benzene while being cooled with ice, whereby white precipitates were deposited immediately. The reaction mixture was washed with a diluted hydrochloric acid, 5% aqueous solution of sodium carbonate and an aqueous solution saturated with sodium chloride, and dried over anhydrous sodium sulfate. Evaporation of benzene gave 4.6 g of oily 3-butynyl α-allyl-α-methoxyphenylacetate, $n_D^{25}$ 1.5137.

| Elementary Analysis | C (%) | H (%) |
|---|---|---|
| Calculated (as C₁₆H₁₈O₃) | 74.39 | 7.02 |
| Found | 74.29 | 6.94 |

EXAMPLE 3

Into a suspension of 0.75 g of 66% sodium hydride-paraffin in 20 cc of dimethylformamide was added a solution of 5.6 g of allyl α-benzyl-α-hydroxyphenylacetate in 10 cc of dimethylformamide under cooling, and the mixture was stirred for 1 hour. Successively, methyl chloride was introduced into the mixture. The reaction mixture was poured in ice-water and the resultant was subjected to extraction with ether. The ether extract was washed with an aqueous solution saturated with sodium chloride, and dried over sodium sulfate. Thereafter, ether was distilled out and paraffin was removed, whereby, 5.1 g oily allyl α-benzyl-α-methoxyphenylacetate, $n_D^{25}$ 1.5488 was obtained.

| Elementary Analysis | C (%) | H (%) |
|---|---|---|
| Calculated (as C₁₉H₂₀O₃) | 77.00 | 6.80 |
| Found | 76.88 | 6.68 |

EXAMPLE 4

Into a solution of 1.1 g of sodium methylate in 20 cc of methanol was added a solution of 6.0 g of allyl α-benzyl-α-chlorophenylacetate in 10 cc of methanol under cooling, and the mixture was stirred for 2 hours, whereby white precipitates were deposited. The reaction mixture was poured in water and the resultant was subjected to extraction with ether. The ether extract was washed with an aqueous solution saturated with sodium chloride and dried over sodium sulfate, and thereafter evaporation of ether gave 5.6 g of oily allyl α-benzyl-α-methoxyphenylacetate, $n_D^{25}$ 1.5486.

| Elementary Analysis | C (%) | H (%) |
|---|---|---|
| Calculated (as C₁₉H₂₀O₃) | 77.00 | 6.80 |
| Found | 76.93 | 6.87 |

EXAMPLE 5

Into a suspension of 1.5 g of 66% sodium hydride-paraffin in 20 cc of dimethylformamide was added a solution of 4.5 g of α-phenyl-α-hydroxyphenylacetic acid in 10 cc of dimethylformamide under cooling, and the mixture was stirred for 1 hour. Successively, 5.8 g of butynyl bromide was added thereto and the stirring was continued for 1 hour. The reaction mixture was poured in ice-water, and the resultant was subjected to extraction with ether. The ether extract was washed with an aqueous solution saturated with sodium chloride, and dried over sodium sulfate. Thereafter ether was distilled out and paraffin was removed to obtain 4.0 g of oily 1-butynyl α-phenyl-α-(1-butynyloxy)phenylacetate, $n_D^{25}$ 1.5581.

| Elementary Analysis | C (%) | H (%) |
|---|---|---|
| Calculated (as C₂₂H₂₀O₃) | 79.49 | 6.06 |
| Found | 79.41 | 6.18 |

EXAMPLE 6

A solution of 4.8 g of α-phenyl-α-methoxyphenylacetic acid, 3.0 g of triethylamine and 4.0 g of tosylate of butynyl alcohol in 20 cc of dimethylformamide was stirred for 2 hours. The reaction mixture was poured into water, and the resultant was subjected to extraction with ether. The extract was washed with sodium bicarbonate solution and aqueous solution saturated with sodium chloride, and dried over sodium sulfate. Evaporation of ether gave 4.3 g of oily 3-butynyl α-phenyl-α-methoxyphenyl acetate, $n_D^{25}$ 1.5574.

| Elementary Analysis | C (%) | H (%) |
|---|---|---|
| Calculated (as C₁₉H₁₈O₃) | 77.53 | 6.16 |
| Found | 77.71 | 6.08 |

EXAMPLE 7

Into a suspension of 0.75 g of 66% sodiumhydrideparaffin in 20 cc of dimethylformamide was added a solution of 3.8 g of α-allyl-α-methoxyphenethylalcohol in 10 cc of dimethylformamide under cooling, and the mixture was stirred for 1 hour. Successively, 2.5 g of propargylbromide was added thereto and the stirring was continued for 1 hour. The reaction mixture was poured in ice-water, and the resultant was subjected to extraction with ether.

The ether extract was washed with an aqueous solution saturated with sodium chloride and dried over sodium sulfate. Thereafter ether was distilled out and paraffin was removed to obtain 3.5 g of oily propargyl α-allyl-α-methoxyphenethylether. $n_D^{25}$ 1.5197.

| Elementary Analysis | C (%) | H (%) |
|---|---|---|
| Calculated (as $C_{15}H_{18}O_2$) | 78.23 | 7.88 |
| Found | 78.16 | 7.79 |

The phenylacetic acid derivatives according to the present invention have prominent synergistic effects on natural pyrethrin as well as allethrin and other various cyclopropanecarboxylic acid ester type insecticides, particularly prominent effect on N-chrysanthemoxymethyl-3,4,5,6-tetrahydrophthalimide (hereinafter referred to as tetramethrin).

In addition, the present phenylacetic acid derivatives are more excellent in the synergistic effect on allethrin, tetramethrin and 5-benzyl-3-furylmethyl chrysanthemate [hereinafter referred to as Chrysron, (a registered trade mark of Sumitomo Chemical Co., LTD.)], compared with that of piperonyl butoxide which has been used most widely among the commercially available synergists.

Further, the present phenylacetic acid derivatives have prominent synergistic effects also on carbamate type insecticides such as carbaryl, and may be useful for the production of an insecticidal composition having broader effects for controlling injurious insects, because of their hormone activities on insects.

The synergistic effects of the present phenylacetic acid derivatives on the cyclopropanecarboxylic acid ester type insecticides and the carbamate type insecticides will be substantiated in the following referential example.

REFERENTIAL EXAMPLE

Each mixture of natural pyrethrin, allethrin, tetramethrin, Chrysron or carbaryl with 5 times amount by weight based on the weight of said active ingredient of piperonyl butoxide or the present compounds (1) to (27), or said active ingredient itself was adjusted to desired test concentration with use of acetone, and the killing effect was measured according to the method in which a small amount of the resulting preparation is attached to dorsum of protharum of housefly adults with use of a microcylinge. As the results, the lethal dose [the amount required for killing 50% of the flies ($LD_{50}$)] is shown in the following table.

Table

| Insecticide | Synergist | | $LD_{50}$ ($\gamma$/Fly) | Ratio of enhancing the killing effect |
|---|---|---|---|---|
| Tetramethrin | — | | 0.530 | 1.0 |
| " | Piperonyl butoxide | | 0.129 | 4.1 |
| " | Present compound | (1) | 0.068 | 7.8 |
| " | " | (2) | 0.061 | 8.7 |
| " | " | (3) | 0.064 | 8.3 |
| " | " | (4) | 0.071 | 7.5 |
| " | " | (5) | 0.042 | 12.5 |
| " | " | (6) | 0.066 | 8.0 |
| " | " | (7) | 0.067 | 7.9 |
| Tetramethrin | Present compound | (8) | 0.128 | 4.5 |
| " | " | (9) | 0.111 | 4.8 |
| " | " | (10) | 0.077 | 6.9 |
| Tetramethrin | — | | 0.520 | 1.0 |
| " | Piperonyl butoxide | | 0.121 | 4.3 |
| " | Present compound | (11) | 0.046 | 11.3 |
| " | " | (12) | 0.052 | 10.0 |
| " | " | (13) | 0.050 | 10.4 |
| " | " | (14) | 0.064 | 8.1 |
| " | " | (15) | 0.060 | 8.7 |
| " | " | (16) | 0.055 | 9.5 |
| " | " | (17) | 0.063 | 8.3 |
| " | " | (18) | 0.047 | 11.1 |
| Tetramethrin | — | | 0.570 | 1.0 |
| " | Piperonyl butoxide | | 0.146 | 3.9 |
| " | Present compound | (19) | 0.067 | 8.5 |
| " | " | (20) | 0.053 | 10.8 |
| " | " | (21) | 0.060 | 9.5 |
| " | " | (22) | 0.056 | 10.2 |
| " | " | (23) | 0.085 | 6.7 |
| " | " | (24) | 0.054 | 10.6 |
| " | " | (25) | 0.065 | 8.8 |
| " | " | (26) | 0.081 | 7.0 |
| " | " | (27) | 0.081 | 7.0 |
| Natural Pyrethrin | — | | 0.400 | 1.0 |
| " | Piperonyl butoxide | | 0.077 | 5.2 |
| " | Present compound | (1) | 0.082 | 4.9 |
| " | " | (3) | 0.079 | 5.1 |
| " | " | (5) | 0.071 | 5.6 |
| Natural Pyrothrin | — | | 0.350 | 1.0 |
| " | Piperonyl butoxide | | 0.071 | 4.9 |
| " | Present compound | (11) | 0.054 | 6.5 |
| " | " | (16) | 0.064 | 5.5 |
| Natural Pyrethrin | — | | 0.390 | 1.0 |
| " | Piperonyl butoxide | | 0.076 | 5.1 |
| " | Present compound | (20) | 0.056 | 7.0 |
| " | " | (24) | 0.058 | 6.7 |
| Allethrin | — | | 0.560 | 1.0 |
| " | Piperonyl butoxide | | 0.175 | 3.2 |
| " | Present compound | (1) | 0.085 | 6.6 |
| " | " | (3) | 0.076 | 7.4 |
| " | " | (5) | 0.057 | 9.8 |
| Allethrin | — | | 0.60 | 1.0 |
| " | Piperonyl butoxide | | 0.167 | 3.6 |

Table-continued

| Insecticide | Synergist | | $LD_{50}$ ($\gamma$/Fly) | Ratio of enhancing the killing effect |
|---|---|---|---|---|
| " | Present compound | (11) | 0.060 | 10.0 |
| " | " | (16) | 0.083 | 7.2 |
| Allethrin | — | | 0.610 | 1.0 |
| " | Piperonyl butoxide | | 0.185 | 3.3 |
| " | Present compound | (20) | 0.062 | 9.8 |
| " | " | (24) | 0.069 | 8.8 |
| Chrysron | — | | 0.026 | 1.0 |
| " | Piperonyl butoxide | | 0.021 | 1.2 |
| " | Present compound | (1) | 0.011 | 2.4 |
| Chrysron | Present compound | (3) | 0.011 | 2.4 |
| " | " | (5) | 0.009 | 2.7 |
| Chrysron | — | | 0.024 | 1.0 |
| " | Piperonyl butoxide | | 0.018 | 1.3 |
| " | Present compound | (11) | 0.008 | 3.0 |
| " | " | (16) | 0.009 | 2.7 |
| Chrysron | — | | 0.027 | 1.0 |
| " | Piperonyl butoxide | | 0.021 | 1.3 |
| " | Present compound | (20) | 0.010 | 2.7 |
| " | " | (24) | 0.013 | 2.1 |
| Carbaryl | — | | 5 or more | 1.0 |
| " | Piperonyl butoxide | | 0.240 | 20.8 or more |
| " | Present compound | (1) | 0.208 | 24.0 " |
| " | " | (3) | 0.194 | 25.8 " |
| " | " | (5) | 0.161 | 31.0 " |
| Carbaryl | — | | 5 or more | 1.0 |
| " | Piperonyl butoxide | | 0.20 | 25 or more |
| " | Present compound | (11) | 0.09 | 56 " |
| " | " | (16) | 0.11 | 45 " |
| Carbaryl | — | | 5 or more | 1.0 |
| " | Piperonyl butoxide | | 0.262 | 19 or more |
| " | Present compound | (20) | 0.120 | 41 " |
| " | " | (24) | 0.128 | 39 " |
| 3,4-Dimethyl-phenyl-N-methyl-carbamate | — | | 5 or more | 1.0 |
| " | Piperonyl butoxide | | 0.836 | 6 or more |
| " | Present compound | (1) | 0.278 | 18 " |
| " | " | (3) | 0.273 | 18 " |
| " | " | (5) | 0.238 | 21 " |
| 3,4-dimethyl-phenyl-N-methyl-carbamate | — | | 5 or more | 1.0 |
| " | Piperonyl butoxide | | 0.63 | 8 or more |
| " | Present compound | (11) | 0.21 | 24 " |
| " | " | (16) | 0.25 | 20 " |
| 3,4-Dimethyl-phenyl-N-methyl-carbamate | — | | 5 or more | 1.0 |
| " | Piperonyl butoxide | | 0.970 | 5 or more |
| " | Present compound | (20) | 0.252 | 19 " |
| " | " | (24) | 0.258 | 19 " |
| — | Present compound | (1) | 2 or more | — |
| — | " | (2) | " | — |
| — | " | (3) | " | — |
| — | " | (4) | " | — |
| — | " | (5) | " | — |
| — | " | (6) | " | — |
| — | " | (7) | " | — |
| — | " | (8) | " | — |
| — | " | (9) | " | — |
| — | Present compound | (10) | 2 or more | — |
| — | " | (11) | " | — |
| — | " | (12) | " | — |
| — | " | (13) | " | — |
| — | " | (14) | " | — |
| — | " | (15) | " | — |
| — | " | (16) | " | — |
| — | " | (17) | " | — |
| — | " | (18) | " | — |
| — | " | (19) | " | — |
| — | " | (20) | " | — |
| — | " | (21) | " | — |
| — | " | (22) | " | — |
| — | " | (23) | " | — |
| — | " | (24) | " | — |
| — | " | (25) | " | — |
| — | " | (26) | " | — |
| — | " | (27) | " | — |

As is clear from the above Referential Example, the present compounds are effective as synergists for cyclopropanecarboxylate type insecticides and carbamate type insecticides, but the scope to which the present compounds may be applied is not limited thereto.

Compositions comprising one or more insecticides of the cyclopropanecarboxylic ester type and the carbamate type, as the active ingredients, and, in addition, one or more phenylacetic acid derivatives of the present invention in an amount of suitable times the weight of said active ingredients, are specifically effective in controlling sanitary pests such as house flies, mosquitoes, cockroaches; rice plant pests such as rice stem borers, plant hoppers, leafhoppers; lepidopterous larvae, which are injurious to fruit-trees and vegetables, such as larvae of cabbage worms, army worms, diamond-back moths, cut worms, etc; plant parasitic mites; pantry pests such as rice weevils, almond moths, etc. Furthermore, said compositions are also effective in controlling other agricultural and sanitary pests, forest pests, and pests for horticulture.

In the preparation of the insecticidal compositions, the active insecticides of the cyclorpopanecarboxylic ester type or the carbamate type, and the novel synergists of phenylacetic acid derivatives may be optionally formulated by use of usual adjuvants for insecticides into any form such as oil sprays, emulsifiable concentrates, wettable powders, dusts, granules, aerosols, mosquito coil, fumigants, dusts or solid preparations containing baits and other attractants, and any other form, although in some cases it is more convenient for formulation to use the active ingredients and synergists dissolved in advance in suitable solvents such as xylene, methyl-naphthalene, acetone, trichloroethane, and the like.

Under certain circumstances, the insecticial activities of said compositions can be further enhanced by simultaneous in corporation with piperonyl butoxide, sulfoxide, safroxane, MGK-264, S-421 and other known synergists for pyrethroids, etc.

Multipurpose compositions can be formulated with said insecticidal compositions by the incorporation with other active ingredients such as organochlorine or organo-phosphorus insecticides, fungicides, miticides, herbicides, fertilizers, and other agricultural chemicals.

The preparative method and the effectiveness of the present insecticidal compositions will be further illustrated in the following Examples 8 to 27, and Test Examples 1 to 12, but it is needless to say that these examples are not intended to limit the scope of the present invention.

EXAMPLE 8

A mixture of 0.05 part of tetramethrin respectively together with each of 0.25 part of the present compounds (1) to (27) was dissolved individually in 2 parts of xylol, and the resultant was made the whole 100 parts with deodorized kerosene, whereby each oil spray was obtained.

EXAMPLE 9

A solution of 0.05 part of N-chrysanthemoxymethyl-dimethylmaleimide, 0.15 part of the present compound (5) and 0.1 part of piperonyl butoxide in 5 parts of xylol was made the whole 100 parts with deodorized kerosene, whereby the oil spray was obtained.

EXAMPLE 10

A mixture of 0.1 part of 3-phenoxybenzyl chrysanthemate respectively together with each of 0.5 part of the present compounds (2), (3), (5), (11), (16) and (20) was dissolved individually in 2 parts of xylol, and the resultant was made the whole 100 parts with deodorized kerosene, whereby each oil spray was obtained.

EXAMPLE 11

A mixture of 0.05 part of Chrysron respectively together with each of 0.25 part of the present compounds (2), (3), (5), (11), (13), (20) and (24) was dissolved individually in 2 parts of xylol, and the resultant was made the whole 100 parts with deodorized kerosene, whereby each oil spray was obtained.

EXAMPLE 12

A solution of 0.035 part of tetramethrin, 0.015 part of Chrysron and 0.15 part of the present compound (11) in 2 parts of xylol was made the whole 100 parts with deodorized derosene, whereby the oil spray was obtained.

EXAMPLE 13

A mixture of 1.5 parts of pyrethrum extract (containing 20% of pyrethrin), 1.5 parts of the present compound (2), 1 part DDT, 5 parts of xylol and 6 parts of deodorized kerosene was introduced into an aerosol vessel, and a valve portion was equipped to the vessel. Thereafter, 85 parts of a propellent (a liquified petroleum gas) was introduced under a pressure through the said valve portion, whereby the aerosol was obtained.

EXAMPLE 14

A mixture of 0.35 part of the d-trans isomer of tetramethrin, 0.05 part of Chrysron, 1 part of the present compound (12), 6.6 parts of xylol and 7 parts of deodorized kerosene was introduced into an aerosol vessel, and a valve portion was equipped to the vessel. Thereafter, 85 parts of the same propellent as mentioned in Example 11 was introduced under a pressure through the valve portion, whereby the aerosol was obtained.

EXAMPLE 15

A mixture of 0.3 part of tetramethrin, 0.2 part of 3-phenoxybenzyl d-trans chrysanthemate, 0.5 part of piperonyl butoxide, 0.5 part of the present compound (5), 12.5 parts of deodorized kerosene, and 1 part of an emulsifier Atmos 300 (a registered trade mark of Atlas Chem. Co.) was emulsified in 50 parts of pure water, and the resulting emulsion was introduced together with 35 parts of a mixture consisting of deodorized butane and deodorized propane (3 : 1) into an aerosol vessel, whereby the water base aerosol was obtained.

EXAMPLE 16

A mixture of 0.3 part of tetramethrin respectively together with each of 1.5 parts of the present compounds (2), (3), (5), (11) and (20) was dissolved individually in 20 parts of acetone, and the resultant was stirred and mixed sufficiently with 98.2 parts of 300 mesh diatomaceous earth in a mixing and grinding machine. Successively, evaporation of acetone gave each dust.

EXAMPLE 17

A mixture of 1 part of Meobal (3,4-dimethylphenyl-N-methylcarbamate) respectively together with each of 3 parts of the present compounds (5), (12) and (20) was dissolved individually in 20 parts of acetone, and the resultant was mixed sufficiently under stirring with 796 parts of 300 mesh talc in a mixing and grinding machine. Thereafter, evaporation of acetone gave each dust.

EXAMPLE 18

A mixture of 1 part of Bassa (2-sec-butylphenyl N-methylcarbamate) respectively together with each of 2 parts of the present compounds (5), (11) and (20) was dissolved individually in 20 parts of acetone, and the resultant was mixed under stirring with 797 parts of 200 mesh talc in a mixing and grinding machine. Thereafter, evaporation of acetone gave each dusts.

EXAMPLE 19

A mixture of 5 parts of 5-propargylfurfuryl chrysanthemate, 20 parts of the present compound (2), 15 parts of Sorpol SM-200 (Trade mark of an emulsifier produced by Toho Chemical Co.) and 60 parts of xylol was mixed and dissolved under stirring to obtain the emulsifiable concentrate.

EXAMPLE 20

A mixture of 5 parts of d-trans insomer of Allethrin, 25 parts of the present compound (13), 15 parts of Sorpol SM-200, and 55 parts of xylol was mixed and dissolved under stirring to obtain the emulsifiable concentrate.

EXAMPLE 21

A mixture of 5 parts of dl-cis isomer of Chrysron, 25 parts of the present compound (16), 15 parts of Sorpol SM-200, and 55 parts of xylol was mixed and dissolved each other under stirring to obtain the emulsifiable concentrate.

EXAMPLE 22

A mixture of 15 parts of tetramethrin, 5 parts of d-trans isomer of Chrysron, 30 parts of the present compound (22), 5 parts of Sorpol SM-200 and 45 parts of 300 mesh talc was mixed sufficiently under stirring in a mixing and grinding machine to obtain the wettable powder.

EXAMPLE 23

A mixture of 0.4 g of allethrin respectively together with each of 1.2 g of the present compounds (5), (11), (16) and (22) was dissolved individually in 20 ml of methanol, and the resultant was mixed homogeneously with 98.4 g of a carrier for a mosquito coil (a mixture of tabu powder, marc and wood powder in the ratio of 3 : 5 : 1). After the methanol was evaporated, 150 ml of water was added thereto, and the resultant was kneaded sufficiently, formulated and dried, whereby each mosquito coil was obtained.

EXAMPLE 24

A mixture of 0.2 g of 5-propargyl-α-ethynylfuryl 2',2'-dimethylcyclopropanecarboxylate and 0.8 g of the present compound (5) was dissolved in a suitable amount of chloroform, and the resulting solution was adsorbed in a surface of asbestos having an area of 2.5 cm × 1.5 cm and a thickness of 0.3 mm. Another asbestos having the same area and thickness as mentioned above was attached on the foregoing asbestos.

Thus, the fibrous insecticidal fumigant for an electric heating plate was obtained. There may be used other fibrous materials than asbestoes such as pulp and the like, which have the effect equivalent to that of asbestos.

EXAMPLE 25

A mixture of 15 parts of 3'-phenoxybenzyl-2,2,3,3-tetramethylcyclopropane-1-carboxylate, 35 parts of the present compound (3), 5 parts of Sorpol SM-200 and 45 parts of 300 mesh talc was stirred sufficiently in a mixing and grinding machine, whereby the wettable powder was obtained.

EXAMPLE 26

A mixture of 5 parts of 5-propargyl-2-methyl-3-furylmethyl chrysanthemate, 15 parts of the present compound (13), 2 parts of 0,0-dimethyl-0-(3-methyl-4-nitrophenyl)thiophosphate, 10 parts of Sorpol SM-200 and 68 parts of xylol was dissolved each other under stirring, whereby the emulsifiable concentrate was obtained.

EXAMPLE 27

A mixture of 5 parts of dimethrin, 15 parts of the present compound (16), 5 parts of Toyolignin CT (Trade mark of Toyobo Co.) and 75 parts of GSM Clay (Zeaklite Co.) was mixed sufficiently each other in a mixing and grinding machine. Water was added thereto in an amount of 10% of said mixture, and the resulting mixture was granulated by means of a granulator and air-dried, whereby the granule was obtained.

Insecticidal activities of the present composition prepared above are substantiated in the following Test Examples.

TEST EXAMPLE 1

According to Campbell's turn table method [Soap and Sanitary Chemicals, Vol. 14, No. 6, 119 (1938)], 5 ml of each of the oil sprays obtained in Example 7 was sprayed, and one group of about 100 house fly adults was exposed to the descending mist for 10 minutes. Successively, the flies were fed and transferred in a thermostat to be allowed to stand at 27°C, and after 24 hours, 90% or more of the flies was killed by any oil spray.

On the other hand, the test was made on 0.05% oil spray prepared according to the same procedure in Example 6 using singly tetramethrin to know the killing ratio of 52%. Therefore the synergistic effect of the present compounds was confirmed.

TEST EXAMPLE 2

According to the procedure similar to that of Test Example 1, the tests were made on the insecticidal effects of the oil sprays obtained in Examples 8, 9, 10 and 11, whereby 90% or more of house flies was killed after 24 hours by each oil spray.

TEST EXAMPLE 3

According to the aerosol test method using Peet Grady's chamber (bft)³ [Soap and Chemical Specialities, Blue Book (1965)], the tests were made on insecticidal effects to house fly adults concerning the aerosols obtained in Examples 12, 13 and 14 and the results were as shown in the following table.

| Composition | Amount sprayed g/1000ft³ | Knock down ratio (%) 5 min. | 10 min. | 15 min. | Mortality (%) |
|---|---|---|---|---|---|
| Aerosol of Example 12 | 3.0 | 29 | 69 | 85 | 73 |

| Composition | Amount sprayed g/1000ft³ | Knock down ratio (%) 5 min. | 10 min. | 15 min. | Mortality (%) |
|---|---|---|---|---|---|
| Aerosol of Example 13 | 3.1 | 42 | 81 | 97 | 94 |
| Water base aerosol of Example 14 | 3.0 | 36 | 80 | 93 | 87 |

TEST EXAMPLE 4

To the bottom of a glass Petri dish of 14 cm in diameter, each of the dusts obtained in Examples 15 and 16 was uniformly dusted in a proportion of 2 g/m², and butter was coated on the lower part of the dish, leaving an uncoated portion of 1 cm in width. Subsequently, a group of about 10 adults of German cockroaches was liberated in the dish and contacted with the dust for 10 minutes, thereafter the cockroaches were transferred to another vessel, were fed and were allowed to stand for 3 days, whereby 90% or more of the cockroaches was killed.

TEST EXAMPLE 5

Onto young rice plants grown in a flower pot having about 2.5 inch of diameter, which had elapsed about 20 days after sowing, the dusts obtained in Examples 15, 16 and 17 were dusted in an amount ratio of 300 mg/pot with use of a bell jar duster, and the whole was, 4 minutes thereafter, covered with a wire net. About 20 brown leafhopper adults were liberated therein, whereby 90% or more of the leafhoppers was killed after 24 hours by any dust.

TEST EXAMPLE 6

Into a (70 cm)³ glass chambers about 50 house fly adults were liberated, and 0.7 ml of each emulsion prepared by diluting the emulsifiable concentrates obtained in Example 18, 19 and 20, to 50 times with water, was sprayed under 20 lb by means of a glass atomizer, whereby 90% or more of the house flies was knocked down within 10 minutes. On next day, 90% or more of the house flies knocked down was killed.

TEST EXAMPLE 7

Rice plants which had elapsed 45 days after sowing were grown in a 1/50,000 Wagner pot, and the emulsion prepared by diluting the emulsifiable concentrates obtained in Example 20, to 200 times with water, and the dilution prepared by diluting the wettable powders obtained in Examples 21 and 24, to 500 times with water were sprayed respectively thereto in an amount ratio of 10 ml/pot. The whole was covered with a wire net and thereafter about 30 green rice leafhopper adults were liberated therein, whereby 90% or more of the leafhoppers was killed after a day.

TEST EXAMPLE 8

Into a (70 cm)³ glass chamber, about 50 northern house mosquito adults were liberated, and the mosquito coils which were obtained in Example 22 and which were ignited on both ends, were placed respectively in the glass chamber, whereby 80% or more of the mosquitoes was knocked down within 20 minutes by any coils.

TEST EXAMPLE 9

Into a (70 cm)³ gass chamber, about 50 house fly adults were lilerated, and the insecticidal fumigant for heating obtained in Example 23 was placed on an electric heating plate to be fumigated under heating in the chamber, whereby 80% or more of the house flies was knocked down within 20 minutes.

TEST EXAMPLE 10

The emulsifiable concentrates obtained in Examples 19 and 25 were diluted to 40,000 times with water, and 2 liters of the resulting emulsion was introduced into a polystyrene case having 23 × 30 cm of area and 6 cm of depth. About 100 full grown larvae of northern house mosquitoes were liberated therein, whereby 90% or more of the larvae was killed on next day by each emulsion.

TEST EXAMPLE 11

Into a 14 liter volume polyethylene backet, was put 10 liters of water, and 0.5 g of the granule obtained in Example 26 was added. After a day, about 100 full grown larvae of northern house mosquitoes were liberated therein. As the results, it was observed that 90% or more of the larvae was killed within 24 hours.

TEST EXAMPLE 12

Into 100 g of unhulled rice, was mixed under sufficient stirring 100 mg of each dust obtained in Examples 15, and the mixture was put into 100 ml Erlenmeyer flask. About 50 rice weevils were liberated therein, and the flask was covered and allowed to stand for a week, whereby 80% or more of rice weevils was killed.

What is claimed is:

1. A compound of the formula,

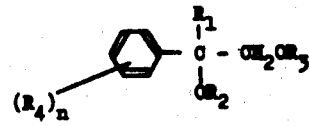

wherein $R_1$ is a $C_{1-6}$ alkyl, a $C_{2-6}$ alkenyl, a $C_{3-6}$ alkynyl, a $C_{3-6}$ cycloalkyl or benzyl, $R_2$ is a $C_{1-6}$ alkyl, a $C_{3-6}$ alkenyl or a $C_{3-6}$ alkynyl, $R_3$ is a $C_{1-6}$ alkyl, a $C_{3-6}$ alkenyl or a $C_{3-6}$ alkynyl, (provided that $R_2$ is a $C_{3-6}$ alkynyl when $R_3$ is a $C_{1-6}$ alkyl), $R_4$ is hydrogen, halogen, a $C_{1-4}$ alkyl or methylenedioxy, and n is an integer of 1 to 5.

2. A compound of the formula,

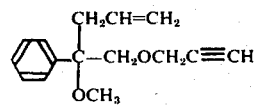

* * * * *